US011350908B2

(12) United States Patent
Martin et al.

(10) Patent No.: US 11,350,908 B2
(45) Date of Patent: Jun. 7, 2022

(54) THREE-DIMENSIONAL ULTRASOUND IMAGING WITH SLOW ACQUISITION DATA LINK AND ASSOCIATED DEVICES, SYSTEMS, AND METHODS

(71) Applicant: KONINKLIJKE PHILIPS N.V., Eindhoven (NL)

(72) Inventors: William Robert Martin, Westford, MA (US); McKee Dunn Poland, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 183 days.

(21) Appl. No.: 16/498,906

(22) PCT Filed: Mar. 29, 2018

(86) PCT No.: PCT/EP2018/058044
§ 371 (c)(1),
(2) Date: Sep. 27, 2019

(87) PCT Pub. No.: WO2018/178220
PCT Pub. Date: Oct. 4, 2018

(65) Prior Publication Data
US 2021/0085290 A1  Mar. 25, 2021

Related U.S. Application Data

(60) Provisional application No. 62/478,827, filed on Mar. 30, 2017.

(51) Int. Cl.
*A61B 8/00* (2006.01)
*A61B 8/08* (2006.01)

(52) U.S. Cl.
CPC .......... *A61B 8/4281* (2013.01); *A61B 8/4472* (2013.01); *A61B 8/483* (2013.01); *A61B 8/5207* (2013.01); *A61B 8/565* (2013.01)

(58) Field of Classification Search
CPC ... A61B 8/4281; A61B 8/4472; A61B 8/5207; A61B 8/565; A61B 8/483
See application file for complete search history.

(56) References Cited

U.S. PATENT DOCUMENTS 5,029,016 A * 7/1991 Hiyama .............. H04N 1/2179
358/403
5,976,088 A  11/1999 Urbano et al.
(Continued)

FOREIGN PATENT DOCUMENTS

WO  0079300 A1  12/2000

OTHER PUBLICATIONS

E. Modiano, "A Simple Analysis of Average Queueing Delay in Tree Networks," IEEE Transactions on Information Theory, vol. 42, No. 2, pp. 660-664, Mar. 1996 (Year: 1996).*
(Continued)

*Primary Examiner* — Oommen Jacob
*Assistant Examiner* — Nyrobi Celestine (57) ABSTRACT

Ultrasound image devices, systems, and methods are provided. In one embodiment, an ultrasound imaging system includes an ultrasound imaging probe configured to acquire image data associated with an object at an acquisition data rate; and a communication interface in communication with the ultrasound imaging probe and configured to transmit a first subset of the image data in real time based on the acquisition data rate; and transmit a second subset of the image data at a delayed time. In one embodiment, a method of ultrasound imaging includes acquiring, by an ultrasound imaging probe, image data associated with an object at an acquisition data rate; transmitting, to a host via a communication link, a first subset of the image data in real time based on the acquisition data rate; and transmitting, to the
(Continued)

host via the communication link, a second subset of the image data at a delayed time.

19 Claims, 9 Drawing Sheets

(56) References Cited

U.S. PATENT DOCUMENTS

| | | | |
|---|---|---|---|
| 6,914,882 B2* | 7/2005 | Merani | H04L 47/24 |
| | | | 370/230 |
| 6,969,352 B2 | 11/2005 | Chiang et al. | |
| 9,152,585 B2* | 10/2015 | Ware | G06F 13/161 |
| 9,367,517 B2* | 6/2016 | Jones | H04L 49/109 |
| 10,025,531 B2* | 7/2018 | Yoon | G06F 3/0659 |
| 10,063,895 B2* | 8/2018 | Makovetzky | H04N 21/2385 |
| 10,193,831 B2* | 1/2019 | Peled | H04L 49/9063 |
| 2006/0058658 A1* | 3/2006 | King | H04L 69/32 |
| | | | 600/437 |
| 2007/0161904 A1 | 7/2007 | Urbano | |
| 2016/0066893 A1 | 3/2016 | Cho et al. | |
| 2017/0086798 A1* | 3/2017 | Bjaerum | A61B 8/4472 |
| 2018/0078145 A1* | 3/2018 | Sato | A61B 5/0095 |
| 2020/0257720 A1* | 8/2020 | Rahme | A61B 6/563 |

OTHER PUBLICATIONS

International Search Report for International Application No. PCT/EP2018/058044, filed Mar. 29, 2018, 3 pages.

Written Opinion of the International Searching Authority for International Application No. PCT/EP2018/058044, filed Mar. 29, 2018, 7 pages.

* cited by examiner

THREE-DIMENSIONAL ULTRASOUND IMAGING WITH SLOW ACQUISITION DATA LINK AND ASSOCIATED DEVICES, SYSTEMS, AND METHODS

RELATED APPLICATIONS

This application is the U.S. National Phase application under 35 U.S.C. § 371 of International Application No. PCT/EP2018/058044, filed on Mar. 29, 2018, which claims the benefit of Provisional Application Ser. No. 62/478,827, filed Mar. 30, 2017. These applications are hereby incorporated by reference herein.

TECHNICAL FIELD

The present disclosure relates generally to ultrasound imaging and, in particular, to transferring three-dimensional (3D) ultrasound image data from an ultrasound imaging probe over a bandwidth-limited data link to a host for live 3D imaging and subsequent review.

BACKGROUND

Ultrasound imaging systems are widely used for medical imaging. Both two-dimensional (2D) and 3D imaging of bodies of patients is known to provide a reliable tool for medical practitioners to view parts of a patient's anatomy without the need for any surgical step. In 3D ultrasound imaging, or volume imaging, the acquisition of a 3D image may be accomplished by conducting 2D scans that slice through the volume of interest. Hence, a multitude of 2D images is acquired that lie next to another. By proper image processing, a 3D image of the volume of interest can be constructed from the multitude of 2D images. The 3D information acquired from the multitude of 2D images is displayed in proper form on a display for the user of the ultrasound system. In some clinical applications, live 3D imaging or four-dimensional (4D) imaging may be used to provide clinicians with a real-time view of moving parts of the anatomical site, for example, a beating heart or other tissue.

Ultrasound imaging systems are complete stations that may be fixed to a certain location and are often movable on rollers to provide flexible use in different locations. The ultrasound imaging systems may include an acquisition subsystem, a signal processing subsystem, display devices, and user interface (UI) devices. The acquisition subsystem may include one-dimensional (1D) or 2D transducer arrays that send high-frequency acoustic waves into a patient's body and records the echoes as the acoustic waves are reflected back by the organs and/or surrounding tissues of the patient. The reflected echoes define the size, shape, and mass of the tissues and/or organs of the patient. The transducer arrays may be motorized reciprocating planar or curved arrays or micro-beamformed matrix arrays. The signal processing subsystem creates images from the echo signals for display on the display devices. The UI devices allow a clinician to interact with the ultrasound imaging system to obtain images that are relevant for the medical diagnosis.

In 3D imaging systems, the acquisition subsystem is typically integrated into the same physical and electrical infrastructure as the signal processing subsystem, the display device, and the UI devices. Thus, the data transfer within the ultrasound imaging system, for example, from the acquisition subsystem to the display devices, may have an unconstrained bandwidth. For example, the acquisition subsystem, the signal processing subsystem, and the display devices may be interconnected by parallel input/output (I/O) on printed circuit boards and may include gigabit (Gbit) serial I/O circuits and internal cables. For example, the ultrasound imaging system may include a probe including the acquisition subsystem. With advanced processing technologies, the probe may also include the signal processing subsystem. The probe may transfer image data to external display devices for display, for example, via cables. Such ultrasound imaging system may be costly and the probe cables can be cumbersome to handle during medical imaging.

One approach to reducing the cost of the ultrasound imaging system and increasing the flexibility for use is to employ a low-power, low-cost universal serial bus (USB) interface or a wireless interface, such as Bluetooth, ultra-wide band (UWB), and Institute of Electrical and Electronics Engineers (IEEE) 802.11 WiFi, for transferring image data from the probe to the display devices. In addition, with the recent advances in mobile technologies, the display devices can include a mobile phone or a tablet with a USB connection or a wireless connection. However, the USB interface or the wireless interface may have a limited bandwidth or transfer throughput, for example, in the range of a few megabits per second (Mbps) to a few hundreds Mbps. 3D imaging typically uses multi-line techniques to create a large number of scan lines per acoustic event. Live 3D imaging requires the probe to transfer the large number of scan lines to the display devices as soon as possible, for example, instantaneously or within a short period of time. Thus, the lost-cost, low-power, bandwidth-limited interface may not be compatible with current methods of real-time or live 3D imaging.

SUMMARY

While existing ultrasound imaging systems have proved useful, there remains a need for improved systems and techniques for providing low-cost, low-power live 3D imaging. Embodiments of the present disclosure provide mechanisms for a clinician to view a sufficient amount of live 3D scans of a volume under examination while buffering full detailed scans of the volume for subsequent review. For example, an ultrasound imaging probe can include transducer arrays and a processing component. The transducer arrays emit acoustic waves towards a volume inside a patient's body and receive echo signals reflected by the volume. The processing component processes the received echo signals to produce image data representing the volume. The processing component prioritizes the image data for transfer to a host for display. The processing component identifies high-priority image data from a set of image data. The probe transfers or streams the high-priority image data to the host for real-time display and concurrently stores low-priority image data locally for delayed transfer to the host. The high-priority data can include a multi-planar image, a cut plane (C-plane) image, a sub-sampling of the volume, or a full-sampling of a portion of the volume. The high-priority image data may be transferred in real time using a fraction of the bandwidth needed for transferring a full-sampling of the entire volume. The host may combine the real-time transferred high-priority image data and the delayed transferred low-priority image data to reconstruct a full image of the volume for subsequent review.

In one embodiment, an ultrasound imaging system is provided. The ultrasound imaging system includes an ultrasound imaging probe configured to acquire image data associated with an object at an acquisition data rate; and a communication interface in communication with the ultrasound imaging probe and configured to transmit a first subset of the image data in real time based on the acquisition data rate; and transmit a second subset of the image data at a delayed time.

In some embodiments, the communication interface includes a transfer bandwidth less than an acquisition data bandwidth of the image data at the acquisition data rate. In some embodiments, the communication interface is further configured to transmit the first subset of the image data using a portion of the transfer bandwidth and transmit the second subset of the image data using a remaining portion of the transfer bandwidth. In some embodiments, the communication interface is at least one of a wired serial interface or a wireless interface. In some embodiments, the ultrasound imaging probe includes a memory configured to store the second subset of the image data while the communication interface is transmitting the first subset of the image data. In some embodiments, the ultrasound imaging probe includes a processing component configured to identify the first subset of the image data from the acquired image data. In some embodiments, the ultrasound imaging probe includes a memory configured to include a first queue and a second queue, wherein the first queue has a higher transmission priority than the second queue, and wherein the processing component is further configured to queue the first subset of the image data in first queue; and queue the second subset of the image data in second queue. In some embodiments, the communication interface is further configured to transmit the first subset of the image data from the first queue based on the acquisition data rate; and transmit the second subset of the image data from the second queue at the delayed time. In some embodiments, the first subset of the image data includes a plurality of scan lines associated with the object, and wherein the plurality of scan lines is associated with an image plane. In some embodiments, the first subset of the image data includes data samples representative of a depth window within a plurality of scan lines associated with the object, and wherein the data samples are associated with a C-plane.

In one embodiment, a method of ultrasound imaging is provided. The method includes acquiring, by an ultrasound imaging probe, image data associated with an object at an acquisition data rate; transmitting, to a host via a communication link, a first subset of the image data in real time based on the acquisition data rate; and transmitting, to the host via the communication link, a second subset of the image data at a delayed time.

In some embodiments, the communication link includes a transfer bandwidth less than an acquisition data bandwidth of the image data at the acquisition data rate. In some embodiments, the transmitting the first subset of the image data includes transmitting the first subset of the image data using a portion of the transfer bandwidth of the communication link, and wherein the transmitting the second subset of the image data includes transmitting the second subset of the image data using a remaining portion of the transfer bandwidth. In some embodiments, the method further includes storing, at a memory of the ultrasound imaging probe, the second subset of the image data concurrently with the transmitting the first subset of the image data. In some embodiments, the method further includes identifying, by a processing component of the ultrasound imaging probe, the first subset of the image data from the acquired image data. In some embodiments, the method further includes queuing, at a memory of the ultrasound imaging probe, the first subset of the image data in a first queue; and queuing, at the memory, the second subset of the image data in a second queue, wherein the first queue has a higher transmission priority than the second queue, wherein the transmitting the first subset of the image data includes transmitting the first subset of the image data from the first queue based on the acquisition data rate, and wherein the transmitting the second subset of the image data includes transmitting the second subset of the image data from the second queue at the delayed time. In some embodiments, the first subset of the image data includes a plurality of scan lines associated with the object, and wherein the plurality of scan lines is associated with an image plane. In some embodiments, the first subset of the image data includes data samples representative of a depth window within a plurality of scan lines associated with the object, and wherein the data samples are associated with a C-plane. In some embodiments, the method further comprises displaying, at the host, a real-time image based on the first subset of the image data. In some embodiments, the method further includes combining, at the host, the first subset of the image data and the second subset of the image data to form a combined image; and storing, at the host, the combined image for subsequent review.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 1:
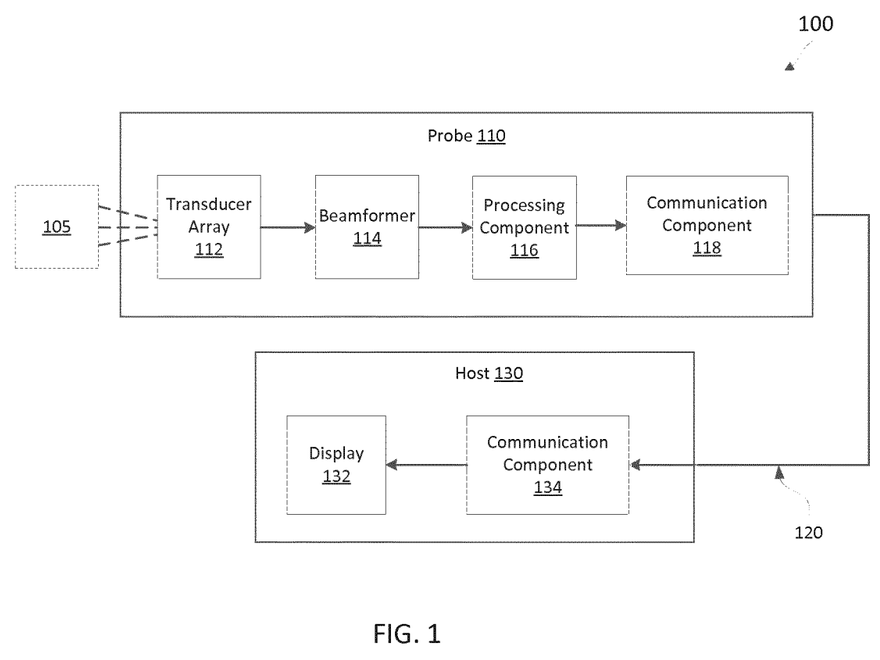
FIG. 1 is a schematic diagram of an ultrasound imaging system, according to aspects of the present disclosure.

FIG. 1 is a schematic diagram of an ultrasound imaging system 100, according to aspects of the present disclosure. The system 100 is used for scanning an area or volume 105 of a patient's body. The system 100 includes an ultrasound imaging probe 110 in communication with a host 130 over a communication interface or link 120. The probe 110 includes a transducer array 112, a beamformer 114, a processing component 116, and a communication component 118. The host 130 includes a display 132 and a communication component 134.

The transducer array 112 emits ultrasound signals towards an anatomical object or volume 105 and receives echo signals reflected from the volume 105 back to the transducer array 112. The transducer array 112 may include acoustic elements arranged in a one-dimensional (1D) array or in a two-dimensional (2D) array, as described in greater detail herein. The beamformer 114 is coupled to the transducer array 112. The beamformer 114 controls the transducer array 112, for example, for transmission of the ultrasound signals and reception of the ultrasound echo signals. The beamformer 114 provides image signals to the processing component 116 based on the response or the received ultrasound echo signals. The beamformer 114 may include multiple stages of beamforming. The beamforming can reduce the number of signal lines for coupling to the processing component 116, as described in greater detail herein.

The processing component 116 generates image data from the image signals. The processing component 116 may be implemented as a combination of software components and hardware components. In an embodiment, the processing component 116 may be implemented on a field programmable gate array (FPGA) and may include programmable state machines to control the processing and conversion of the image signals to the image data. For example, the processing component 116 may perform filtering and/or quadrature demodulation to condition the image signals. The processing component 116 may perform analytic detection on the filtered signals, for example, envelope detection. The processing component 116 may logarithmically compresses the detected signals to a suitable dynamic range for further processing. The processing component 116 may perform further post-filtering and/or smoothing on the detected signal to facilitate decimation, which may reduce the number of data samples, for example, by a factor of about 2 or about 5 to about 10. The processing component 116 may prepare image data from the decimated signals for display, for example, at the display 132. The processing component 116 may prepare 2D tomographic slices of the volume 105 to be displayed or may convert or render the image data into a 3D image for display.

The communication component 118 is coupled to the processing component 116. The communication component 118 transmits the image data to the host 130 via the communication link 120. At the host, the communication component 134 may receive the image data and the display 132 (e.g., a monitor) may display the image data. The communication link 120 may be any suitable communication link. In an embodiment, the communication link 120 may be a low-speed link for power, size, and cost reductions. For example, the communication link 120 can be a wired serial link or interface, such as a USB link. Alternatively, the communication link 120 can be a wireless link, such as a UWB link, an IEEE 802.11 WiFi link, or a Bluetooth link. The communication components 118 and 134 may implement data encoding, data decoding, modulation, demodulation, and/or protocol processing according to a communication protocol of the communication link 120.

Figure 2:
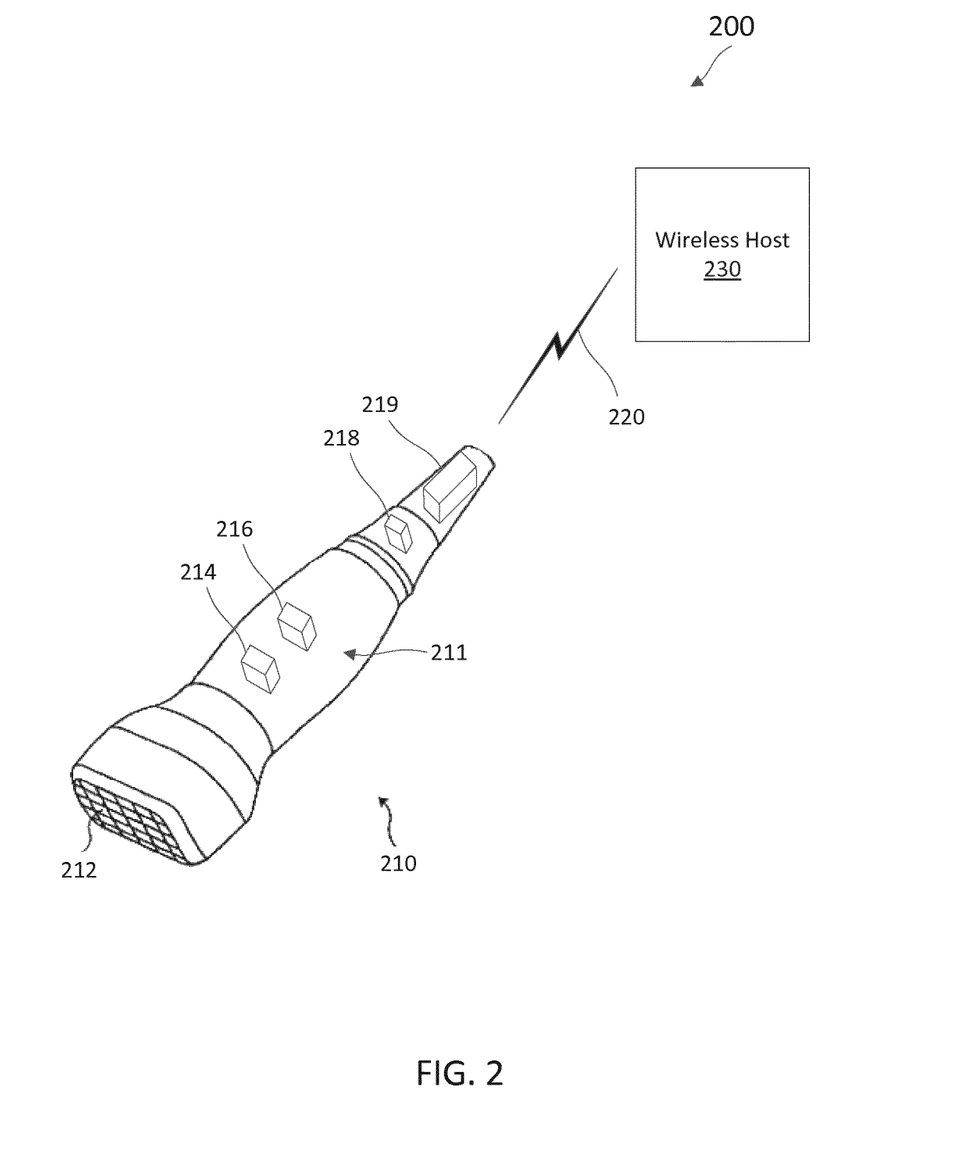
FIG. 2 is a schematic diagram illustrating a wireless ultrasound imaging system, according to aspects of the present disclosure.

FIG. 2 is a schematic diagram illustrating a wireless ultrasound imaging system 200, according to aspects of the present disclosure. The system 200 is similar to the system 100 and provides an example of a wireless ultrasound imaging probe 210 in communication with a wireless host 230 over a wireless link 220. The wireless link 220 may be a Bluetooth link, a UWB link, a WiFi link, or any suitable link for wireless communication. The wireless probe 210 may be substantially similar to the probe 110. For example, the wireless probe 210 includes a probe housing 211 housing a transducer array 212 similar to the transducer array 112, a beamformer 214 similar to the beamformer 114, a processing component 216 similar to the processing component 116.

The wireless probe 210 further includes a wireless transceiver 218 and an antenna corresponding to the communication component 118. For example, the wireless transceiver 218 may implement a wireless communication protocol, such as a Bluetooth, WiFi, or UWB protocol. The wireless transceiver 218 may wirelessly transmit image data acquired by the wireless probe 210 via the antenna to the wireless host 230 for display. The wireless host 230 may be substantially similar to the host 130.

The wireless probe 210 further includes a battery pack 219 providing power to the components in the wireless probe 210 for scanning. In some embodiments, the wireless probe 210 may further include user input devices (e.g., push buttons) for user controls and/or visual display devices (e.g., light emitting diodes (LEDs) and a display screen) for indications or notifications of certain events. In some embodiments, the wireless transceiver 218, the antenna, the battery pack 219, the user input devices, and/or the display devices may be configured as a plug-in module that can be plugged into the wireless probe 210.

Figure 3:
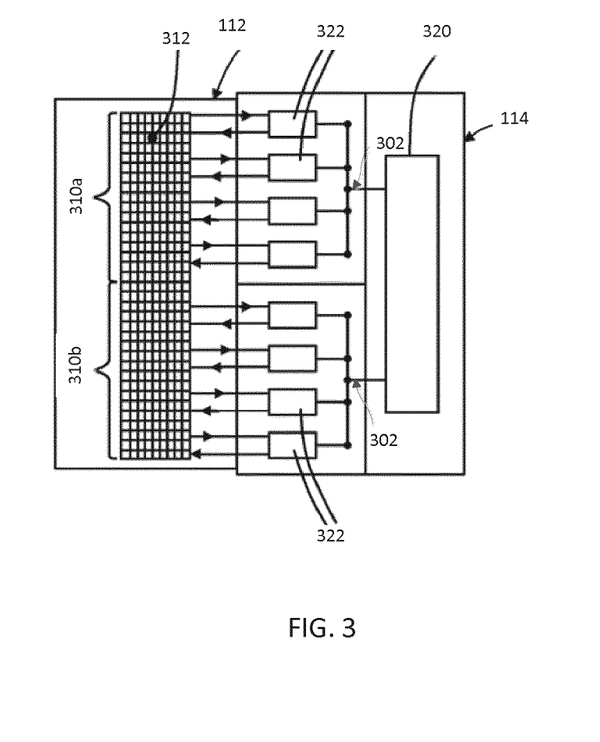
FIG. 3 is a schematic diagram illustrating a detailed view of a transducer array and a beamformer, according to aspects of the present disclosure.

FIG. 3 is a schematic diagram illustrating a detailed view of the transducer array 112 and the beamformer 114, according to aspects of the present disclosure. The transducer array 112 includes a plurality of acoustic elements 312. The beamformer 114 includes a plurality of micro-beamformers 322 and a main beamformer 320.

The acoustic elements 312 transmit ultrasound signals towards a volume (e.g., the volume 105) and receive echo signals reflected from the volume. In some embodiments, the transducer array 112 may include thousands of acoustic elements 312 forming a multitude of sub-arrays 310a and 310b. For illustrative purposes, merely two sub-arrays are shown. However, the number of sub-arrays may be greater than two, for example, about eight or more. The acoustic elements 312 may be arranged in a 2D array. For example, the acoustic elements 312 can be arranged as a rectangular matrix as shown or alternatively arranged in a different shape, such as a square, curved, oval, or circular shape, to provide optimal scanning. The shape can be arranged according to the object under examination and the clinical application.

The micro-beamformers 322 control both the transmission and reception of acoustic pulses through the acoustic elements 312. The micro-beamformers 322 performs beamforming by combining the acoustic responses (e.g., the echoes). Each micro-beamformer 322 is connected to a single acoustic element 312 and configured to perform beamforming for the connected acoustic element 312. The micro-beamformers 322 are grouped into sub-arrays 310. For example, neighboring or nearby micro-beamformers 322 may be grouped together into a sub-array 310. The outputs of micro-beamformers 322 within a sub-array 310 are combined to produce a beamformed output, which is partially beamformed with respect to the entire array. While FIG. 3 illustrates two groups of four micro-beamformers 322, each group may include any suitable number of micro-beamformers 322, for example, about eight or about sixteen. In some particular embodiments, the beamformer 114 may include eight groups each having sixteen micro-beamformers 322. The outputs of the micro-beamformers 322 within each sub-array 310 may be summed to form a sub-array group output 302. The sub-array group output 302 is then coupled to the main beamformer 320, described in more detail below.

There are two main phases of beamforming, namely, transmit and receive. During the transmit phase, the acoustic elements 312 emits acoustic pulses towards a volume of interest (e.g., the volume 105). For transmit beamforming, the acoustic elements 312 transmit a set of time-delayed acoustic pulses to generate a focus in the 3D space of the medium or volume.

During the receive phase, the acoustic elements 312 receive echoes of the acoustic pulses reflected by various points of the volume. For receive beamforming, the received echoes are delayed, amplified, and combined. The received echoes may be delayed by static delays, meaning they are unchanged during the course of acoustic reception. Alternatively, the receive delays may be programmable. For example, the receive delays may be dynamically configured to maintain a constant array focus as the echoes propagate through the medium. The separately delayed received signals are summed together, for example, by summers. After the summing, variable gain amplifiers perform time gain compensation. Time variable gain is required because the signals received by the acoustic elements 312 from later times correspond to deeper depths of the body, and are therefore more attenuated. The variable gain amplifiers compensate for the attenuation by increasing the amplitude of the output. The sub-array summed acoustic signals (e.g., the outputs 302) are coupled to the main beamformer 320. The main beamformer 320 performs static or dynamic beamforming to generate a set of fully beamformed image signals for the entire acoustic array (or the portion of the array which is programmed to be active for a particular scan line.) Hence, one main beamformer 320 sub-groups a multitude of micro-beamformers 322. By this, the number of signals from the beamformer 114 to the processing component 116 may be significantly reduced. In some embodiments, the main beamformer 320 can be implemented on the same FPGA as the processing component 116.

Figure 4:
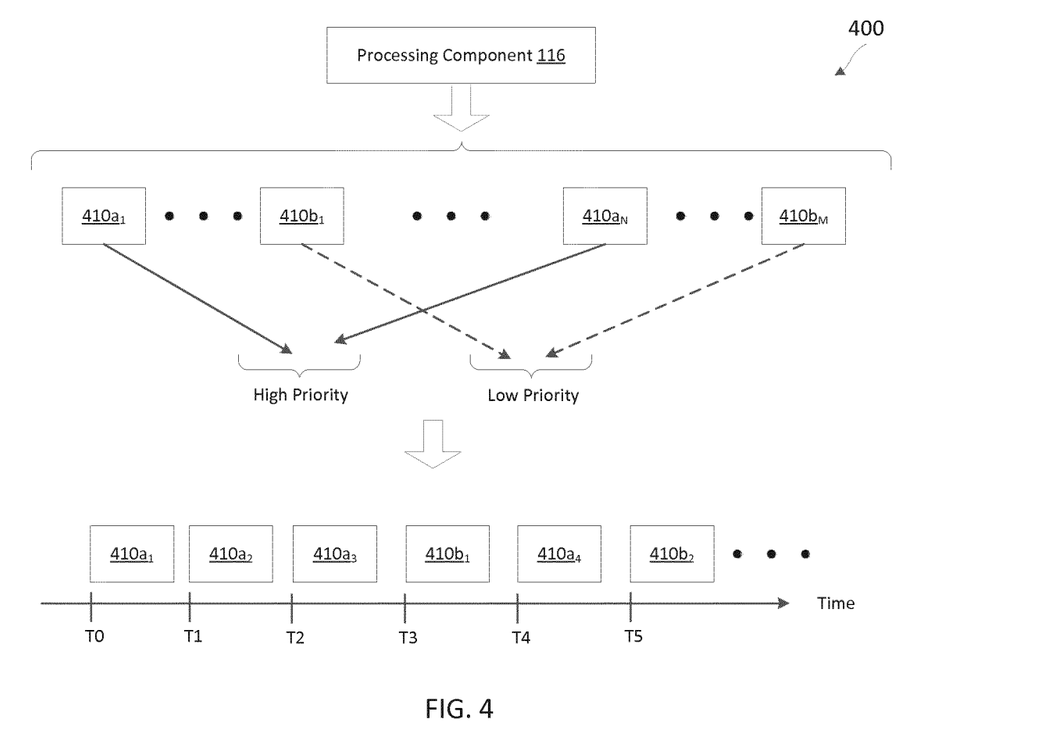
FIG. 4 is a schematic diagram illustrating a priority-based acquisition data transfer scheme, according to aspects of the present disclosure.

FIG. 4 is a schematic diagram illustrating a priority-based acquisition data transfer scheme 400, according to aspects of the present disclosure. The scheme 400 can be employed by the ultrasound imaging probes 110 and 210 to transfer image data over a bandwidth-limited or slow-speed communication link (e.g., the links 120 and 220) in real time for live 3D imaging.

As an example, the processing component 116 generates image data 410 at an acquisition data rate, denoted as $f_{acq}$, based on beamformed image signals. The image data 410 may represent a full-sampling of a volume of interest (e.g., the volume 105). A full-sampling of the volume may include high-resolution scan lines and with high-resolution samples. The acquisition data rate $f_{acq}$ may be greater than a supported data transfer rate of the communication link 120. In other words, the communication link 120 has a transfer bandwidth less than the acquisition data bandwidth at the acquisition data rate $f_{acq}$. For example, transferring the image data 410 in real time may require a bandwidth on the order of Gbps, while the communication link 120 may support a bandwidth of about 1 Mbps to about 20 Mbps. In an embodiment, the link 120 may be a Bluetooth link with a bandwidth of about 1 Mbps. In another embodiment, the link 120 may be an IEEE 802.11n link with a bandwidth of about 100 Mbps. In yet another embodiment, the link 120 may be a UWB link with a bandwidth of about 200 Mbps.

In the scheme 400, the processing component 116 identifies a minimal subset of the image data 410 (e.g., the image data 410a) for live imaging to provide a clinician with sufficient real-time scanning information or a coarse image, for example, to determine whether the probe 110 is placed at an optimal position for scanning the volume of interest. The subset of the image data 410 for real-time or live imaging may be referred to as high-priority image data 410a (e.g., shown as $410a_1 \ldots 410a_N$). The remaining image data 410b may be used for replay at a later time and may be referred to as low-priority image data 410b (e.g., shown as $410b_1 \ldots 410b_M$). In an embodiment, the image data 410a is selected such that the communication link 120 has a sufficient amount of bandwidth to transfer the high-priority image data 410a in real time. Real-time transfer refers to the continuous transfer of the high-priority image data 410a as the high-priority image data 410a is generated or available. For example, the image data 410a requires a transfer rate at a fraction of the acquisition data rate $f_{acq}$.

In an embodiment, the high-priority image data 410a may include, be representative of, and/or otherwise be associated with a multi-planar image of the volume and the low-priority image data 410b may include remaining multi-planar images, scan line data, and/or scan sample data of the volume, as described in greater detail herein. In another embodiment, the high-priority image data 410a may include a C-plane image of the volume within a certain depth window and the low-priority image data 410b may include remaining C-plane images, scan line data, and/or scan sample data of the volume, as described in greater detail herein. In yet another embodiment, the high-priority image data 410a may include a sparse sampling of the volume and the low-priority image data 410b may include remaining scan line data and/or scan sample data of the volume. In yet another embodiment, the high-priority image data 410a may include a full-sampling of a portion of the volume and the low-priority image data 410b may correspond to a full-sampling of a remaining portion of the volume 105.

The high-priority image data 410a and the low-priority image data 410b may be acquired and generated in any suitable order for optimal acoustics or signal processing. For example, certain scan lines may be scanned first to avoid temporal artifacts independent of the categorization of high-priority image data versus low-priority data image data. In an embodiment, scan lines corresponding to the low-priority image data 410b and high-priority image data 410a may be acquired in an interleaving order. In another embodiment, at least a portion of scan lines corresponding to the low-priority image data 410b may be acquired before the high-priority image data 410a. In yet another embodiment, at least a portion of scan lines corresponding to the high-priority image data 410a may be acquired before the low-priority image data 410b.

The high-priority image data 410a has priority over the low-priority image data 410b for transferring to the host 130. The high-priority image data 410a are transferred to the host 130 in real time, for example, by the communication component 118. The low-priority image data 410b may be transferred to the host 130 in a non-real time mode when there is bandwidth available over the link 120 after the transfer of the high-priority image data 410a. Thus, in some embodiments, the low-priority image data 410b may be transferred at a lower rate than the acquisition data rate of the low-priority image data 410b.

To meet the real-time requirement, the high-priority image data 410a is transferred as soon as the high-priority image data 410a is generated. The low-priority image data 410b may be transferred at a delayed time after the transfer of the high-priority image data 410a has completed. For example, the high-priority image data 410a and the low-priority image data 410b may be transferred in an interleaving order. For example, a block of low-priority image data $410b_1$ can be transmitted in between blocks of high-priority image data $410a_3$ and $410a_4$. As shown, the high-priority image data $410a_1$, $410a_2$, $410a_3$, and $410a_4$ are transferred to the host 130 at time T0, T1, T2, and T4, respectively, and the low-priority image data $410b_1$ and $410b_2$ are transferred when there is remaining bandwidth available, for example, at time T3 and T5, respectively. The transferring of the high-priority image data 410a and the low-priority image data 410b is described in greater detail herein.

Figure 5:
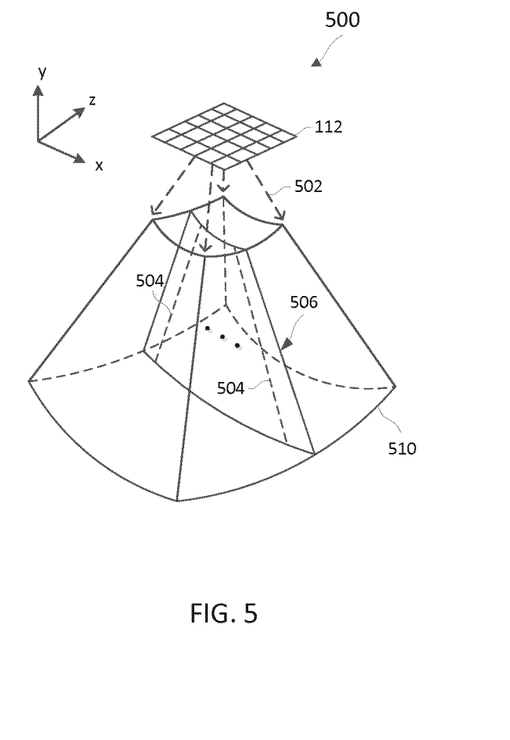
FIG. 5 illustrates a multi-planar imaging scenario for priority-based acquisition data transfer, according to aspects of the present disclosure.

FIG. 5 illustrates a multi-planar imaging scenario 500 for priority-based acquisition data transfer, according to aspects of the present disclosure. The scenario 500 illustrates the prioritizing of image data for a live scan in a multi-planar mode using the scheme 400. In the scenario 500, the transducer array 112 emits beams 502 towards a volume 510 similar to the volume 105 to create scan lines 504 representing the volume 510. Each scan line 504 may include a number of scan samples or sample points. A set of the scan lines 504 may form an image plane 506 in the x-y plane as shown or alternatively in the y-z plane. When applying the scheme 400, the high-priority image data 410a may include a subset of the scan lines 504 or a subset of planes similar to the planes 506 that make up the volume 510. The subset of scan lines 504 may include sparsely spaced samples along the scan lines 504 forming one or more image planes 506 along the z-axis and/or the x-axis. The sparsely spaced image planes 506 may be along the x-axis or the z-axis. The subset can be transferred to a host similar to the host 130 in real time to provide a 3D live scan of the volume 510. The live scan may be a coarse or low-resolution 3D view of the volume 510. The low-priority image data 410b may include remaining scan lines 504 and/or scan samples within the scan lines 504. The remaining scan lines 504 can be transferred to the host at a delayed time. The host can combine the remaining scan lines 504 with the real-time image planes to reconstruct a high-resolution view of the entire volume 510 for subsequent review. For example, the scan samples, scan lines, and/or image planes are time-stamped, and thus the full image can be reconstructed according to the timestamps.

Figure 6:
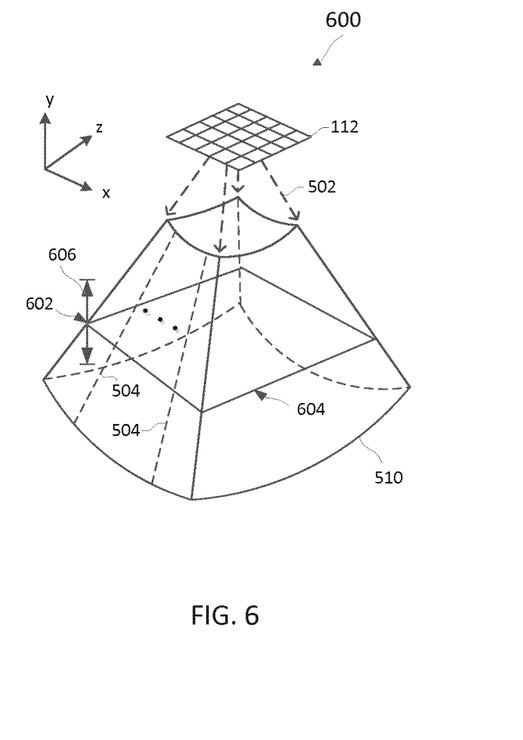
FIG. 6 illustrates a cut plane (C-plane) imaging scenario for priority-based acquisition data transfer, according to aspects of the present disclosure.

FIG. 6 illustrates a C-plane imaging scenario 600 for priority-based acquisition data transfer, according to aspects of the present disclosure. The scenario 600 illustrates the prioritizing of image data for a live scan in a C-plane imaging mode using the scheme 400. In the scenario 600, the transducer array 112 emits beams 502 to create scan lines 504. The data samples from the scan lines 504 at a certain depth 602 forms a C-plane 604 along the x-z plane. In some embodiments, a C-plane 604 may be tilted with respect to the transducer array 112, but generally does not intersect the transducer array 112. When applying the scheme 400, the high-priority image data 410a may include a set of data samples from a depth window 606 within the scan lines 504. The C-planes within the depth window 606 can be transferred to a host similar to the host 130 to provide a 3D live scan of the volume 510 within the depth window 606. The low-priority image data 410b may include remaining scan line samples that are shallower or deeper than the depth window 606. The remaining scan line samples can be transferred to the host at a delayed time. The host can combine the remaining scan line samples with the real-time C-planes to reconstruct a full view of the volume 510 for subsequent review according to timestamps and/or sequence indexes associated with the scan samples.

Figure 7:
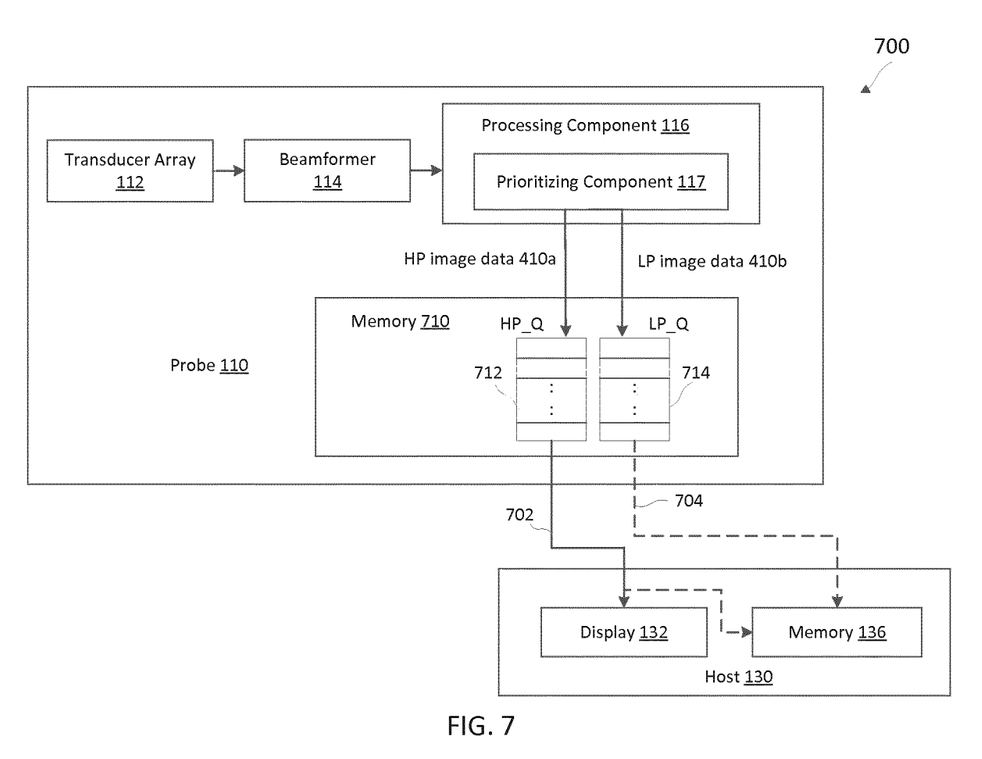
FIG. 7 is a schematic diagram illustrating a priority-based acquisition data transfer scheme, according to aspects of the present disclosure.

FIG. 7 is a schematic diagram illustrating a priority-based acquisition data transfer scheme 700, according to aspects of the present disclosure. The scheme 700 can be employed by the ultrasound imaging probes 110 and 210 to transfer image data or frames over a bandwidth-limited or slow-speed communication link (e.g., the links 120 and 220) for live 3D imaging. The scheme 700 is similar to the scheme 400 and provides a more detailed view of the storing and/or queuing of the high-priority image data 410a and the low-priority image data 410b within the probe 110. In the scheme 700, the processing component 116 may include a prioritizing component 117 that identifies the high-priority image data 410a from a set of 3D image data 410.

The probe 110 may further include a memory 710 coupled to the processing component 116. The memory 710 may include volatile memory and non-volatile memory of any suitable memory types, including random access memory (RAM), read-only memory (ROM), programmable read-only memory (PROM), erasable programmable read-only memory (EPROM), electrically erasable programmable read-only memory (EEPROM), dynamic random-access memory (DRAM), static random-access memory (SRAM), and combinations thereof. In some particular embodiments, the memory 710 may be synchronous dynamic random access memory (SDRAM).

To facilitate the priority-based transfer mechanisms, a portion of the memory 710 can be configured to include a high-priority queue (HP_Q) 712 and another portion of the memory 710 can be configured to include a low-priority queue (LP_Q) 714. The high-priority queue 712 can hold the high-priority image data 410a ready for real-time transmission to the host 130. The low-priority queue 714 can hold the low-priority image data 410b for transmission at a delayed time. The size of the memory 710 may vary depending on the embodiments. In some particular embodiments, the memory 710 may have a size in the range of about 512 megabytes to about 4 gigabytes. In an embodiment, the low-priority queue 714 can have a substantially larger memory space than the high-priority queue 712. In an embodiment, the low-priority queue 714 and the high-priority queue 712 may operate on a first-in-first-out (FIFO) mode.

For example, after the prioritizing component 117 identifies the high-priority image data 410a from the image data 410, the prioritizing component 117 queues the high-priority image data 410a in the high-priority queue 712. The high-priority image data 410a is transferred to the host 130 from the high-priority queue 712 as shown by the arrow 702, for example, via the communication component 118 or the wireless transceiver 218, and displayed at the display 132 in real time. For example, the high-priority image data 410a is held in the high-priority queue 712 for a short period of time and the transfer may be in a continuous streaming mode. The prioritizing component 117 queues or stores the low-priority image data 410b in the low-priority queue 714 while the high-priority image data 410a are being transferred to the host. When the communication link 120 has remaining bandwidth after transferring the high-priority image data 410a or at a subsequent time, the low-priority image data 410b may be continuously transferred to the host 130 in a non-real-time mode as shown by the arrow 704. In other words, the high-priority image data 410a may be transferred using a portion of the bandwidth of the link 120 and the low-priority image data 410b may be transferred using a remaining portion of the bandwidth. As an example, the link 120 may have a bandwidth supporting a transfer throughput of about 10 Mbps. The high-priority image data 410a may require a transfer throughput of about 8 Mbps. Thus, the low-priority image data 410b may be transferred using the remaining about 2 Mbps. In another embodiment, the communication link 120 may be speed up for transferring the high-priority image data 410a and slow-down for transferring the low-priority image data 410b, for example, by applying rate control at the wireless transceiver 218.

In another embodiment, the high-priority image data 410a may be transferred to the host as described above. However, the low-priority image data 410b may be transferred to a non-volatile memory in the probe 210 instead of transferring to the host 130 in concurrent with the high-priority image data 410a. The low-priority image data 410b may be subsequently transferred from the non-volatile memory to the host 130 or another device at a later time for subsequent review, for example, after powering down the probe 210 or relocating the probe 210 after the procedure. For example, a clinician may view the coarse image data (e.g., the high-priority image data 410a) to ensure that data acquisition for a medical examination is performed correctly and an expert may subsequently view and analyze the entire image data including the high-priority image data 410a and the low-priority image data 410b. In some embodiments, the transferring of the low-priority image data 410b at the later time may use a different, higher speed interface than the link 120, for example, a USB interface link.

As shown, the host 130 further includes a memory 136. In some embodiments, the memory 136 may be substantially similar to the memory 710. The memory 136 is configured to store both the high-priority image data 410a and the low-priority image data 410b for subsequent review. For example, upon receiving the low-priority image data 410b, the host 130 may store the low-priority image data 410b in the memory 136 and may combine the low-priority image data 410b with a copy of the high-priority image data 410a to reconstruct a combined image or a full image of the volume for the subsequent review.

Figure 8:
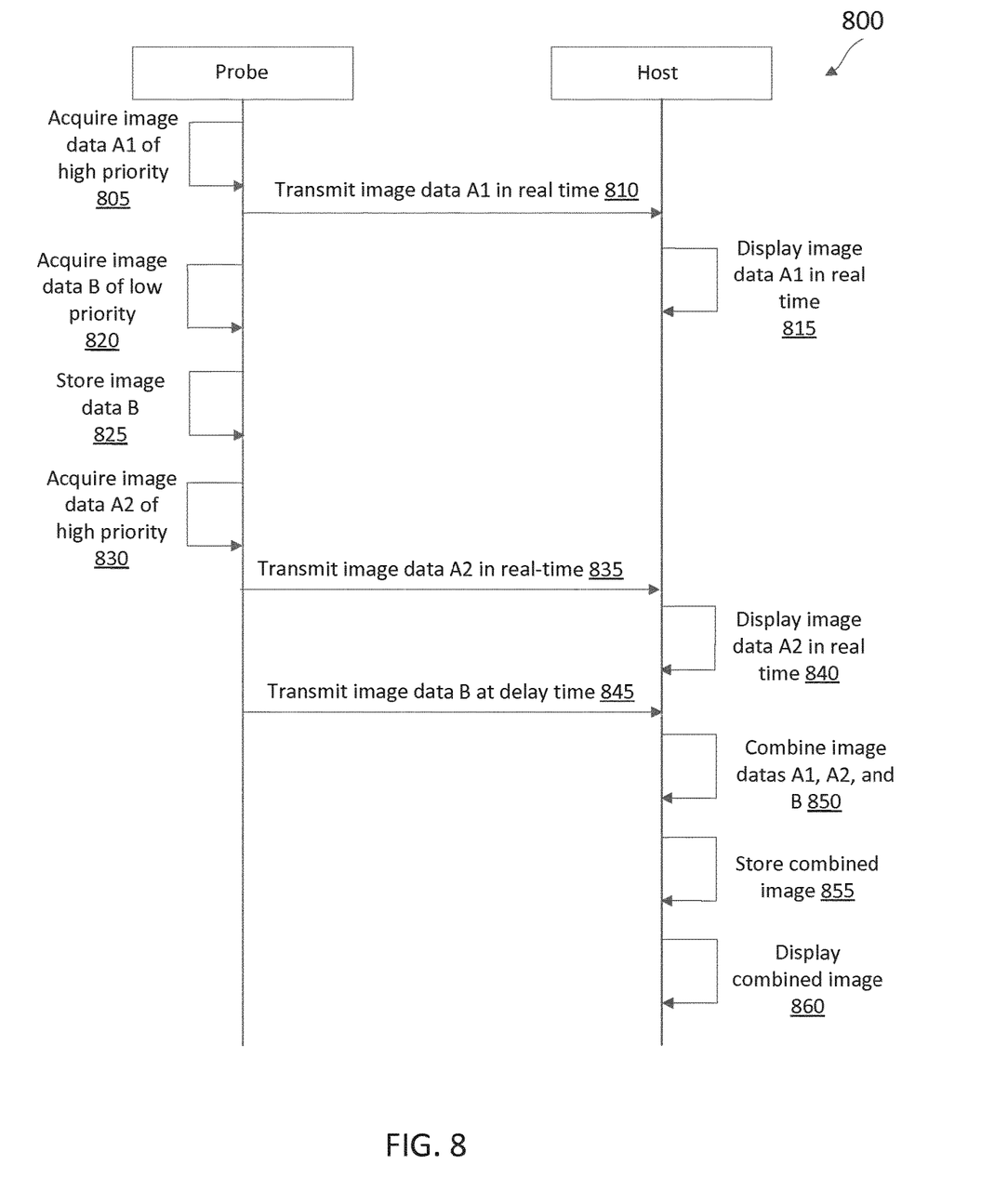
FIG. 8 is a signaling diagram illustrating a priority-based acquisition data transfer method, according to aspects of the present disclosure.

FIG. 8 is a signaling diagram illustrating a priority-based acquisition data transfer method 800, according to aspects of the present disclosure. The method 800 is implemented by an ultrasound imaging probe such as the probes 110 and 210 and a host such as the hosts 130 and 230. The method 800 may employ similar mechanisms as in the schemes 400 and 700 described with respect to FIGS. 4 and 7, respectively. As illustrated, the method 800 includes a number of enumerated steps, but embodiments of the method 800 may include additional steps before, after, and in between the enumerated steps. In some embodiments, one or more of the enumerated steps may be omitted or performed in a different order. While the method 800 is illustrated with two high-priority image data and one low-priority image data for purposes of simplicity of discussion, it will be recognized that embodiments of the present disclosure may scale to many more high-priority image data and low-priority data. Each high-priority image data or low-priority image data may correspond to a subset of scan planes, a subset of scan lines, or a subset of scan sample points of a volume (e.g., the volume 150). The method 800 may begin after selecting a live 3D viewing mode, for example, a multi-planar mode or a C-plane mode as in the scenarios 500 and 600 described with respect to FIGS. 5 and 6, respectively.

At step 805, the probe acquires an image data (e.g., the image data $410a_1$), denoted as A1, of a volume (e.g., the volumes 105 and 510) and identifies the image data A1 as a high-priority data based on the selected live 3D viewing mode. At step 810, the probe transmits the high-priority image data A1 to the host in real time via a communication link (e.g., the links 120 and 220). At step 815, the host displays the high-priority image data A1 in real time on a display (e.g., the display 132).

At step 820, the probe acquires an image data (e.g., the image data $410b_1$), denoted as B, of the volume and identifies the image data B as a low-priority data. For example, the communication link is busy transmitting the image data A1. The step 820 can be performed at the same time as the steps 810 and 815. Thus, at step 825, the probe stores the low-priority image data B in a local memory (e.g., the memory 710). In some embodiments, the steps 810 and/or 815 are performed in concurrent with the steps 820 and/or 825. After the imaging data is obtained, the processing component identifies the high priority subset (e.g., image data A1) and the low priority subset (image data B) from the obtained imaging data.

At step 830, the probe acquires an image data (e.g., the image data $410a_2$), denoted as A2, of the volume and identifies the image data A2 as a high-priority frame. Once the transmission of the image data A1 has completed, the probe continues to transmit the high-priority image data A2 to the host in real time, step 835. At step 840, the host displays the image data A2 in real time on the display.

At step 845, the probe transmits the low-priority image data B to the host at a delayed time when there is available bandwidth after transmitting the high-priority image data A2. In some embodiments, a frame table may be used to describe a single frame, which includes scan lines representing an entire volume. In such embodiments, the frame table can include descriptions or markings indicating that the image data A1 and A2 are for real-time transmission.

At step 850, the host combines a copy of the high-priority image data A1 and A2 with the low-priority data B to reconstruct a combined image or a full image of the volume. At step 855, the host stores the full image in a local memory (e.g., the memory 136). In some embodiments, the full image may be stored according to a cine-loop, which is a looped sequence of images rendered in time. At step 860, the host displays the full image on the display, for example, during a subsequent review.

Figure 9:
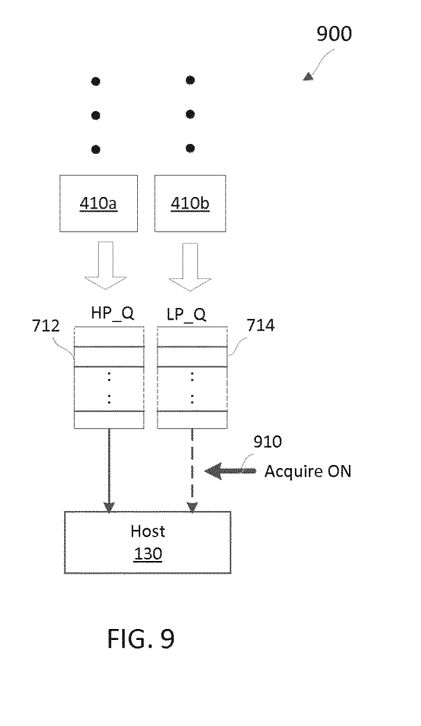
FIG. 9 illustrates a retrospective image capture scenario, according to aspects of the present disclosure.

FIG. 9 illustrates a retrospective image capturing scenario 900, according to aspects of the present disclosure. The scenario 900 illustrates the recording or the capturing of the images when using the schemes 400 and 700. For example, the probe 110 and/or the host 130 may include a user input for capturing or recording an imaging session. In the scenario 900, the high-priority image data 410a may be transferred to the host 130 for real-time display while the low-priority image data 410b are stored in the low-priority queue 714. When a user initiates the acquiring or recording, as shown by the acquire ON arrow 910, the low-priority image data 410 stored in the low-priority queue 714 may be transferred to the host 130 for recording, for example, saved into the memory 136. In some embodiments, the user may select a time duration for the recording, for example, the past few seconds. If the low-priority queue 714 is full when the recording is initiated, new low-priority image data 410b may be discarded, for example, on a FIFO-basis, to allow existing image data in the low-priority queue 714 to be sent to the host. In retrospective capture, the cine loop contains image data already captured. In some cases, the low priority image data may not have been transferred to the host. The host will have to wait for the remaining low priority image data to be transferred before the cine loop can be completed.

Figure 10:
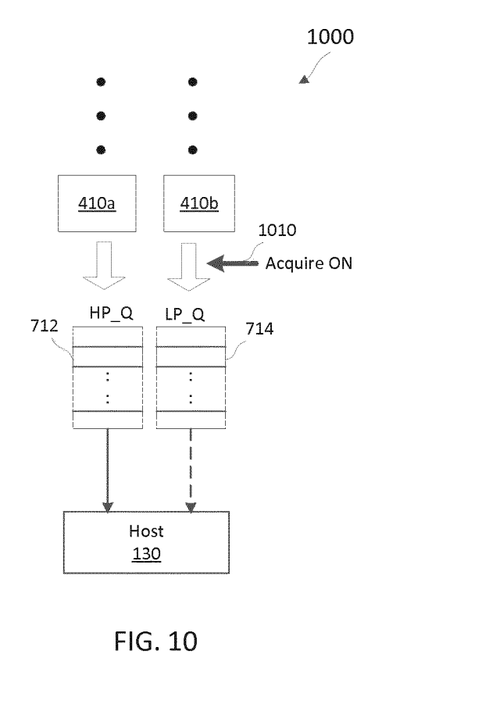
FIG. 10 illustrates a prospective image capture scenario, according to aspects of the present disclosure.

FIG. 10 illustrates a prospective image capturing scenario 1000, according to aspects of the present disclosure. The scenario 1000 illustrates the recording or the capturing of the images when using the schemes 400 and 700. The scenario 1000 may be substantially similar to the scenario 900, but the recording is performed prospectively to record acquired images subsequent to a recording initiation. For example, the queuing of the low-priority image data 410b at the low-priority queue 714 and the transferring of the low-priority image data 410b to the host 130 begins when a user initiates the acquiring or recording, as shown by the acquire ON arrow 1010. In the prospective case, the duration of the recording may be limited by the size of the low-priority queue, since its data cannot be transferred in real time. Recording may halt after the complete consumption of the low-priority queue, at which time transfer from the low-priority queue to the host may complete. In prospective image capture the low priority queue should be flushed at the beginning of the prospective capture since the image data in the queue is not part of the prospective capture and will only delay the completion of the capture.

Figure 11:
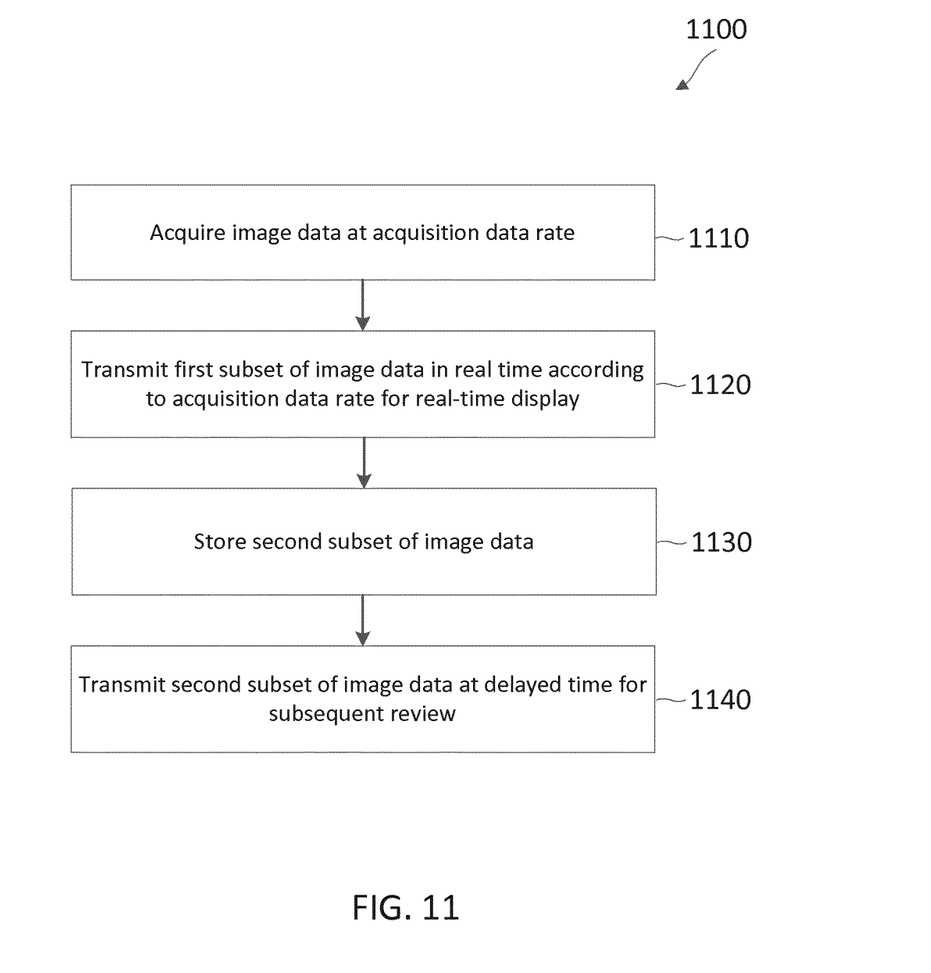
FIG. 11 is a flow diagram of a priority-based acquisition data transfer method, according to aspects of the present disclosure.

FIG. 11 is a flow diagram of a priority-based acquisition data transfer method 1100, according to aspects of the present disclosure. Steps of the method 1100 can be executed by a computing device (e.g., a processor, processing circuit, and/or other suitable component) of an ultrasound imaging probe, such as the probes 110 and 210. The method 1100 may employ similar mechanisms as in the schemes 400 and 600 as described with respect to FIGS. 4 and 6, respectively. As illustrated, the method 1100 includes a number of enumerated steps, but embodiments of the method 1100 may include additional steps before, after, and in between the enumerated steps. In some embodiments, one or more of the enumerated steps may be omitted or performed in a different order.

At step 1110, the method 1100 includes acquiring image data (e.g., a set of 3D image data 410) at an acquisition data rate (e.g., $f_{acq}$).

At step 1120, the method 1100 includes transmitting a first subset (e.g., the high-priority image data 410a) of the image data in real time according to the acquisition data rate, for example, to a host such as the hosts 130 and 230 via a link such as the communication links 120 and 220.

At step 1130, the method 1100 includes storing a second subset (e.g., the low-priority image data 410b) of the image, for example, at a local memory such as the memory 710. The storing may be in concurrent with the transmitting of the first subset.

At step 1140, the method 1100 includes transmitting the second subset of the image data at a delayed time to the host via the link for subsequent review. For example, the second subset may be transmitted when there is bandwidth available over the link after transmitting the first subset.

Aspects of the present disclosure can provide several benefits. For example, the prioritizing of the image data for transfer to the host enables the use of a slow-speed probe-host interface, such as a USB interface or a wireless interface, for real-time or live 3D imaging at a clinically useful frame rate. The use of a USB interface or a wireless interface can improve the flexibility and mobility of the clinician performing the ultrasound imaging. The use of the USB interface or the wireless interface with a real-time streaming display application on a mobile device can reduce the cost and/or the size of ultrasound imaging systems. The real-time transfer of partial image data enable a clinician to view real-time images, such as real-time multi-planar images, real-time C-plane image, or real-time sparse volume images. The real-time images can guide the clinician to obtain an optimal view of the patient's anatomy for 3D image capture. The delay transfer of remaining image data and the combining of the real-time image data and the delayed transferred image data allow the clinician or another expert to review the complete 3D image capture at a later time.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system, comprising:
   an ultrasound imaging probe configured to acquire image data associated with an object at an acquisition data rate;
   a memory comprising a first queue and a second queue; and
   a communication interface in communication with the ultrasound imaging probe and configured to: transmit a first subset of the image data in real time from the first queue based on the acquisition data rate; and transmit a second subset of the image data from the second queue at a delayed time, wherein: the first queue has a higher transmission priority than the second queue; and the ultrasound imaging probe comprises a processor configured to: identify a set of high priority image data as the first subset of the image data and a set of low priority image data as the second subset of the image data; queue the first subset of the image data in the first queue; and queue the second subset of the image data in the second queue.

2. The ultrasound imaging system of claim 1, wherein the communication interface includes a transfer bandwidth less than an acquisition data bandwidth of the image data at the acquisition data rate.

3. The ultrasound imaging system of claim 2, wherein the communication interface is further configured to:
- transmit the first subset of the image data using a portion of the transfer bandwidth; and
- transmit the second subset of the image data using a remaining portion of the transfer bandwidth.

4. The ultrasound imaging system of claim 1, wherein the communication interface is at least one of a wired serial interface or a wireless interface.

5. The ultrasound imaging system of claim 1, wherein the ultrasound imaging probe includes a memory configured to store the second subset of the image data while the communication interface is transmitting the first subset of the image data.

6. The ultrasound imaging system of claim 1, wherein the ultrasound imaging probe includes a processor configured to identify the first subset of the image data from the acquired image data.

7. The ultrasound imaging system of claim 1, wherein the first subset of the image data includes a plurality of scan lines associated with the object, and wherein the plurality of scan lines is associated with an image plane.

8. The ultrasound imaging system of claim 1, wherein the first subset of the image data includes data samples representative of a depth window within a plurality of scan lines associated with the object, and wherein the data samples are associated with a C-plane.

9. A method of ultrasound imaging, the method comprising:
- acquiring, by an ultrasound imaging probe, image data associated with an object at an acquisition data rate;
- providing, in a memory of the ultrasound imaging probe, a first queue and a second queue;
- transmitting, to a host via a communication link, a first subset of the image data from the first queue in real time based on the acquisition data rate; and
- transmitting, to the host via the communication link, a second subset of the image data from the second queue at a delayed time, wherein the method further comprises:
identifying a set of high priority image data as the first subset of the image data and a set of low priority image data as the second subset of the image data; and
- queuing the first subset of the image data in the first queue and the second subset of the image data in the second queue, wherein the first queue has a higher transmission priority than the second queue.

10. The method of claim 9, wherein the communication link includes a transfer bandwidth less than an acquisition data bandwidth of the image data at the acquisition data rate.

11. The method of claim 10, wherein the transmitting the first subset of the image data includes transmitting the first subset of the image data using a portion of the transfer bandwidth of the communication link, and wherein the transmitting the second subset of the image data includes transmitting the second subset of the image data using a remaining portion of the transfer bandwidth.

12. The method of claim 9, further comprising:
- storing, in the memory of the ultrasound imaging probe, the second subset of the image data concurrently with the transmitting the first subset of the image data.

13. The method of claim 9, further comprising:
- identifying, by a processor of the ultrasound imaging probe, the first subset of the image data from the acquired image data.

14. The method of claim 9, wherein the first subset of the image data includes a plurality of scan lines associated with the object, and wherein the plurality of scan lines is associated with an image plane.

15. The method claim 9, wherein the first subset of the image data includes data samples representative of a depth window within a plurality of scan lines associated with the object, and wherein the data samples are associated with a C-plane.

16. The method of claim 9, further comprising displaying, at the host, a real-time image based on the first subset of the image data.

17. The method of claim 16, further comprising:
- combining, at the host, the first subset of the image data and the second subset of the image data to form a combined image; and
- storing, at the host, the combined image for subsequent review.

18. The ultrasound imaging system of claim 1, wherein the memory is a first memory, and the ultrasound imaging system further comprises a host comprising a second memory adapted to store both the first queue and the second queue for subsequent non-real time review.

19. The method of claim 9, wherein the memory is a first memory, and the method comprises storing in a second memory both the first queue and the second queue for subsequent non-real time review.

* * * * *